United States Patent [19]

Garlick et al.

[11] Patent Number: 4,649,039

[45] Date of Patent: Mar. 10, 1987

[54] RADIOLABELING OF METHIONINE-CONTAINING PROTEINS AND PEPTIDES

[75] Inventors: Russell K. Garlick, Townsend; Ludek Jirousek, Tewksbury, both of Mass.

[73] Assignee: E. I. Du Pont de Nemours and Company, Wilmington, Del.

[21] Appl. No.: 627,644

[22] Filed: Jul. 3, 1984

[51] Int. Cl.$^4$ .................... A61K 43/00; G01N 33/536
[52] U.S. Cl. .......................................... 424/1.1; 424/9; 436/542; 530/300; 530/350
[58] Field of Search ................. 424/1.1, 9; 436/542; 260/112 R, 112.5 R; 530/300, 350

[56] References Cited

U.S. PATENT DOCUMENTS

| | | | |
|---|---|---|---|
| 3,957,963 | 5/1976 | Salmon et al. | 424/1.1 |
| 3,959,455 | 5/1976 | Ansari et al. | 424/1.1 |
| 4,260,737 | 4/1981 | Scherberg | 424/1.1 |
| 4,436,718 | 3/1984 | Smith | 424/1.1 |
| 4,448,764 | 5/1984 | Smith et al. | 424/1.1 |
| 4,450,149 | 5/1984 | Kabalka | 424/1.1 |
| 4,473,544 | 9/1984 | Machulla et al. | 424/1.1 |
| 4,476,106 | 10/1984 | Bardy et al. | 424/1.1 |

OTHER PUBLICATIONS

Brot et al, Arch. Biochem. Biophys., 223(1983), 271–281.

*Primary Examiner*—Christine M. Nucker

[57] ABSTRACT

A process for radiolabeling methionine-containing peptides and proteins.

11 Claims, No Drawings

RADIOLABELING OF METHIONINE-CONTAINING PROTEINS AND PEPTIDES

BACKGROUND

The subject invention is a unique, efficient process for radiolabeling methionine-containing peptides and proteins.

Radiolabeled proteins and peptides have been used for some time in the study of many biological systems. Processes for performing such radiolabeling have heretofore proven inefficient in the labeling of proteins and peptides which contain the amino acid methionine due to undesirable oxidation and cleavage of the sulfur residue in methionine. Such oxidation often results in loss of biological activity (Brot and Weissbach, *Arch. Biochemistry and Biophysics*, 223, 271(1983) and, hence, the numerous oxidized forms of the radiolabeled proteins must be separated from the useful, non-oxidized radiolabeled protein. This requires lengthy chromatography procedures which are often unsuccessful.

SUMMARY

The subject invention is an efficient, convenient process for radiolabeling methionine-containing proteins and peptides, particularly with radioactive halogens such as I-125, I-131, I-123, Br-77, or other isotopes such as tritium, P-32 and S-35.

More specifically, the subject invention is a process for the radiolabeling of methionine-containing proteins and peptides comprising the sequential steps of oxidizing the protein or peptide under mild oxidizing conditions to the sulfoxide form, radiolabeling the oxidized protein or peptide; and reducing the radiolabeled sulfoxide form of the protein or peptide under mild reducing conditions back to the native methionine.

DETAILED DESCRIPTION

Methionine is a sulfur-containing amino acid having the chemical formula 2-amino-4-(methylthio)butyric acid [$CH_3SCH_2CH_2CH(NH_2)COOH$]. There are many peptides and proteins which contain methionine residues (MET) which are useful for biological tracer studies including glucagon, methionine enkephalin, beta-endorphin, gastrin substance-P, alpha-bungarotoxin, lysozyme, vasoactive intestinal polypeptide, adrenocorticotropic hormone, human growth hormone, corticotropin releasing factor, growth hormone releasing factor, complement C5A, and others.

The first step in the radiolabeling of methionine-containing proteins or peptides is the mild oxidation of the MET sulfide to its sulfoxide without modification of other amino acids (except possibly cysteine). This reversible step will protect the MET sulfur from further oxidation, cleavage, or from participating in undesirable side reactions during the subsequent radiolabeling step detailing below. The mild oxidation of this first step can be accomplished by any conventional method. The preferred method is the use of hydrogen peroxide in acid media (pH 3-6). This will quantitatively oxidize MET to MET sulfoxide without oxidation of other amino acids such as tryptophan, histidine, phenylalanine and tyrosine. Other methods to oxidize MET to MET sulfoxide use $NaIO_4$, chloramine-T, N-bromosuccinimide, tetranitromethane and organic peroxides. See e.g. N. Shechter et al, *Biochemistry*, 14, 4497(1975) and Hachimori, Y. et al, *Biochem, Biophys. Acta*, 93, 346(1964) herein incorporated by reference.

The second step in the process of the subject invention is the radiolabeling of the oxidized protein or peptide. Although any of the well-known radiolabels can be used for labeling the proteins or peptides contemplated by this invention, labeling by radioiodination is preferred.

Radioiodination is carried out by any of the well-known methods using, e.g. chloramine-T, iodogen, lactoperoxidase, $I_2$ or ICl. The chloramine-T procedure is a modification of the procedure of Hunter et al, *Nature*, 194, 495(1962). This is carried out by incubating a near stoichiometric amount of Chloramine-T with radioactive NaI, (I-125, I-131, I-123), with the pre-oxidized peptide at pH 7.4 in aqueous buffer. The iodogen procedure is carried out by incubating 1,3,4,6-tetrachloro-3α, 6α, diphenylglycouril, radioactive NaI, aqueous buffer (pH 7.4), and the pre-oxidized peptide. The lactoperoxidase procedure is carried out by incubating lactoperoxidase at pH 5-8 in aqueous buffer with radioactive NaI, dilute $H_2O_2$, and the pre-oxidized peptide. The $I_2$ procedure is carried out by incubating radioactive $I_2$ with the pre-oxidized peptide in aqueous buffer at pH 7.4, or in an organic solvent such as ethanol. The ICl procedure is carried out by incubating radioactive ICl with the pre-oxidized peptide in aqueous buffer (pH 7.4) or in an organic solvent such as ethanol. Tritiation is carried out by catalytic reductive dehalogenation with tritium in aqueous or organic solvent. Acylation or conjugation reactions may be used to incorporate any of the above isotopes $^{125}I$, $^{131}I$, $^{123}I$, $^{77}Br$, $^{3}H$, $^{32}P$, $^{35}S$ or others. The acylation or conjugation to the protein or peptide converted to the methionine sulfoxide, rather than to the protein or peptide containing the methionine residue, might be desireable in certain situations.

The third step of the process of the subject invention is the reduction is the MET sulfoxide back to the sulfide. The preferred method of reduction is carried out using a mild reducing agent such as mercaptoacetic acid, mercaptoacetamide, dithiothreitol, or similar reagents (see e.g. Houghten and Li, Methods in Enzymology, 91 549(1983). As a preferred embodiment, mercaptoacetic acid at a concentration of about 1M, in the presence of ethanol and aqueous buffer at 37° C. for 18 hours will reduce MET sulfoxide to the sulfide in about 90% yield.

Following the reduction step, the radiolabeled protein or peptide is purified by HPLC, column or ion exchange chromatography, electrophoresis or other suitable techniques. A purification step can also be performed before and/or after the radiolabeling step. Such additional purifications are preferred in processes for radiolabeling peptides such as glucagon.

As detailed in the Examples below, the process as described above results in the radiolabeling of proteins and peptides in good yields. Further, these radiolabeled proteins and peptides retain substantially all associated biological activity, are chemically defined, and are more homogeneous than products obtained using other methods.

EXAMPLE I

This example demonstrates the utility of the process of the subject invention in the radioiodination of the peptide glucagon (hyperglycemic-glycogenolytic factor; straight-chain polypeptide with a M.W. of about 3500).

Native glucagon was first oxidized to glucagon MET sulfoxide by $H_2O_2$. To 350 μgm glucagon dissolved in 350 μl 1% acetic acid was added a 10 fold molar excess $H_2O_2$ ($9.7 \times 10^{-7}$ moles). The vial was shielded from light and stored at 20° C. for 24 hours. The glucagon met sulfoxide was then purified by reverse phase C-18 HPLC using gradient elution system I. Solvent A was 0.1% trifluoracetic acid in $H_2O$ and solvent B was acetonitrile. The gradient ran from about 20% B to about 40% B in 1 hour. Any protein or peptide reverse phase column which separates glucagon from glucagon sulfoxide may be used but the preferred column is the Vydac C-18 330 Å pore RP.

The glucagon sulfoxide fraction (80-90% yield) was collected and taken to dryness by lyophilization. The glacagon sulfoxide was then dissolved in dilute acetic acid. The protein concentration was determined by spectrophotometry.

The radioiodination was then carried out as follows. To 20 μgm glucagon sulfoxide ($5.7 \times 10^{-9}$ moles) in about 20 μl was added 2 mCi $Na^{125}I$ ($9 \times 10^{-10}$ moles) in 100 μl 0.5M $Na_2HPO_4$(pH7.4). To this was added 5 μgm chloramine-T ($2.2 \times 10^{-8}$ moles) in 5 μl $H_2O$. The radioiodination proceeded for about 2 minutes at ambient temperature and was then stopped by the addition of sodium metabisulfite (5 μgm in 5 μl $H_2O$).

The entire reaction mixture was then purified by HPLC according to the gradient elution process described above, and the monoiodinated glucagon sulfoxide was collected and concentrated to about 0.5 ml by high vacuum. The yield was about 1.2 mCi (60%).

Ethanol (200 μl) and mercaptoacetic acid (200 μl) were added to the monoiodo glucagon sulfoxide. The vial was capped and incubated at 37°-40° C. overnight. The reduction mixture was then flash evaporated to 200 μl by high vacuum in 10-15 minutes, and 1.5-2.0 ml of $H_2O$ was added and the entire mixture purified by HPLC according to the gradient elution process described above and the radioiodinated glucagon sulfide separated. The yield of radioiodinated glucagon was about 350 μuCi (30%). The glucagon was stored in a buffer containing bovine serum albumin, 1-propanol and beta-mercaptoethanol.

The radiochemical purity as determined by analytical HPLC was greater than 97%. The specific activity was carrier free (2200 Ci/mmole) and the radioiodinated glucagon was shown to retain biological activity in a whole liver cell receptor assay and in radioimmunoassay.

EXAMPLE II

This example illustrates the utility of the subject invention on the methionine-containing peptide corticotropin releasing-factor (CRF).

CRF is a hypothalmic peptide hormone which stimulates the secretion of adrenocorticotropic hormone (ACTH) and β-endorphin from the adenohyphophysis. The molecular weight of human-CRF is 4760 and it contains two methionine residues.

The radiolabeling of CRF according to the subject invention was carried out as follows: 400 μg CRF ($8.4 \times 10^{-8}$ moles) in 0.5 ml sodium phosphate buffer (pH 3.0) 0.05M, and 68 μgm $H_2O_2$ ($2 \times 10^{-1}$ moles) in 0.5 ml $H_2O$ were combined in a sealed vial and incubated at 37° C. for 24 hours. The CRF methionine sulfoxide was purified by HPLC according to gradient elution system II. Solvent A was 0.1% trifluoracetic acid and Solvent B was 0.33% trifluoracetic acid-:Acetonitrile (v:v) (30:70). The gradient proceeded from 30% B to 55% B in 100 minutes. The CRF MET sulfoxide was collected and taken to dryness by lyophilization.

The radioiodination of CRF MET sulfoxide was carried out as follows: to 50 μgm CRF $1.05 \times 10^{-8}$ moles in 0.2 ml sodium phosphate buffer (0.1M) (pH 7.0), was added 5.0 mCi $Na^{125}I$, in 0.05 ml sodium phosphate buffer (0.5M) (pH 7.4) and 2.5 μgm chloramine-T ($1.1 \times 10^{-8}$ moles) in 0.01 ml $H_2O$. The reaction proceeded for 5 minutes at ambient temperature and was stopped by the addition of 10 μg sodium metabisulfite in 0.01 ml $H_2O$. The entire reaction mixture was purified by HPLC according to gradient elution system II as described above with the gradient extended from 30% B to 60% B. The radioiodinated CRF MET sulfoxide (about 2.5 mCi/50% yield) was collected and diluted to a final concentration of 20% (by volume) with mercaptoacetic acid. The final volume was about 5 ml. The reduction proceeded at 37°-40° C. in a sealed vial overnight. The mixture was then concentrated to less than 0.5 ml by high vacuum, redissolved in $H_2O$ to 2 ml and purified by HPLC according to gradient elution system II as described above with the gradient extended from 30% B to 60B. The reduced, radioiodinated CRF methionine sulfide (about 1.5 mCi, 50% yield) was collected into a buffer containing bovine serum albumin and β-mercaptoethanol. The radiochemical purity of radioiodinated CRF was determined to be greater than 95%, and was shown to be useful in a radioimmunoassay procedure.

EXAMPLE III

This example illustrates the utility of the process for the peptide growth hormone releasing factor (GHRF).

GHRF is methionine-containing peptide hormone with a MW of 5040. It is from the hypothalamus and causes the release of growth hormone from the pituitary.

The radioiodination of GHRF according to the subject invention proceeded as follows:

To human GHRF, $1.5 \times 10^{-8}$ moles in 0.1 ml 0.1% acetic acid, was added 0.01 ml $H_2O_2$ ($1.5 \times 10^{-5}$ moles). The methionine oxidation reaction proceeded for 18-20 hours at ambient temperature. The GHRF methionine sulfoxide was then purified by gradient HPLC system III using a Vydac reverse phase C-18 (330 Å) column eluted with a gradient that proceeded from 20% $CH_3CN$:80% 0.01M triethyl ammonium phosphate (pH 2.8) to 90% $CH_3CN$:10% 0.01M Triethyl ammonium phosphate (pH 2.8) in about 1 hour. The purified GHRF methionine sulfoxide was taken to dryness by lyophilization.

To about 40 μgm of dry GHRF methionine sulfoxide ($7.9 \times 10^{-9}$ moles) was added 200 μl 0.5M $Na_2 HPO_4$ buffer (pH 7.4), 3 mCi $Na^{125}I$ ($1.4 \times 10^{-9}$ moles) and 10 μgm chloramine T ($4.4 \times 10^{-8}$ moles) in 10 μl $H_2O$. The iodination reaction proceeded for 45 seconds and was stopped by the addition of sodium metabisulfite (10 μgm) in 10 μl $H_2O$. The iodo($^{125}I$) GHRF methionine sulfoxide was then purified by HPLC according to the gradient HPLC system III described above. The yield is about 660 μCi (22%).

The iodo GHRF methionine sulfoxide (660 μCi) was concentrated to about 200 μl by a high vacuum evaporation. 200 μl of mercaptoacetic acid was added and the reduction allowed to proceed overnight at room temperature. The iodo($^{125}I$) GHRF methionine was then purified by gradient HPLC system III as described above with the final yield being about 100 mCi (15%).

What is claimed is:

1. A process for the radiolabeling of methionine-containing proteins or peptides comprising the sequential steps of (i) oxidizing the proteins or peptide under mild oxidizing conditions to the sulfoxide form; (ii) radiolabeling the oxidized protein or peptide; and (iii) reducing the radiolabeled oxidized protein or peptide under mild reducing conditions.

2. The process of claim 1 wherein the oxidation step (i) is carried out using a member of the group consisting of hydrogen peroxide, NaIO$_4$, chloramine-T, N-bromosuccinimide tetranitromethane and organic peroxides.

3. The process of claim 1 wherein the radiolabeling of step (ii) is radioiodination.

4. The process of claim 3 wherein the radioiodination is carried out using a member of the group consisting of a chloramine-T procedure, in iodogen procedure, a lactoperoxidase procedure, and I$_2$ procedure and an ICl procedure.

5. The process of claims 1,2,3 or 4 wherein the reduction of step (iii) is carried out using a member of the group consisting of mercaptoacetic acid, mercaptoacetamide, and dithiothreitol.

6. The process of claim 5 wherein the methionine-containing compound is selected from the group consisting of glucagon, methionine enkephalin, beta-endorphin, gastrin, substance P, alpha-bringarotoxin, lysozyme, vasoactive intestinal polypeptide, andrenocorticotropic hormone (CRF), human growth hormone, corticotropin releasing factor, growth hormone (GHRF) releasing factor and complement C5A.

7. The process of claim 5 wherein the methionine-containing compound is glucagon, GHRF or CRF.

8. The process of claim 6 further including HPLC purification of the radiolabeled composition resulting from step (ii).

9. The process of claim 6 further comprising (iv) purifying by chromatography the radiolabeled reduced composition resulting from step (iii).

10. The process of claim 5 further comprising (iv) purifying by chromatography the radiolabeled reduced composition resulting from step (iii).

11. The process of claim 1 wherein the radiolabeling of step (ii) is carried out using a member of the group consisting of tritium, P-32 and S-35, and any isotope of Br.

* * * * *